US011612588B1

(12) United States Patent
Patterson et al.

(10) Patent No.: US 11,612,588 B1
(45) Date of Patent: *Mar. 28, 2023

(54) CHLORINATED TETRALIN COMPOUNDS AND PHARMACEUTICAL COMPOSITIONS

(71) Applicant: SpringWorks Therapeutics, Inc., Stamford, CT (US)

(72) Inventors: Kristin Patterson, Stamford, CT (US); Mark Hatcher, Stamford, CT (US)

(73) Assignee: Spring Works Therapeutics, Inc., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/937,990

(22) Filed: Oct. 4, 2022

Related U.S. Application Data

(63) Continuation of application No. 17/860,682, filed on Jul. 8, 2022, now Pat. No. 11,504,354.

(60) Provisional application No. 63/365,125, filed on May 20, 2022, provisional application No. 63/263,635, filed on Nov. 5, 2021, provisional application No. 63/241,844, filed on Sep. 8, 2021.

(51) Int. Cl.
*A61K 31/417* (2006.01)
*A61K 9/20* (2006.01)

(52) U.S. Cl.
CPC .............. *A61K 31/417* (2013.01); *A61K 9/20* (2013.01)

(58) Field of Classification Search
None
See application file for complete search history.

(56) References Cited

U.S. PATENT DOCUMENTS

| | | | |
|---|---|---|---|
| 7,342,118 | B2 | 3/2008 | Brodney et al. |
| 7,795,447 | B2 | 9/2010 | Brodney et al. |
| 7,951,958 | B2 | 5/2011 | Brodney et al. |
| 10,590,087 | B1 | 3/2020 | Greer et al. |
| 10,710,966 | B1 | 7/2020 | Greer et al. |
| 11,504,354 | B1 * | 11/2022 | Patterson ............. A61K 31/417 |

FOREIGN PATENT DOCUMENTS

| | | | | |
|---|---|---|---|---|
| WO | WO-0049037 | A1 | 8/2000 | |
| WO | WO-0210141 | A1 | 2/2002 | |
| WO | WO-2005092864 | A1 | 10/2005 | |
| WO | WO-2018045273 | A2 | 3/2018 | |
| WO | WO-2019053727 | A1 | 3/2019 | |
| WO | WO-2021029854 | A1 * | 2/2021 | ........... C07D 233/88 |

OTHER PUBLICATIONS

CAS Registry No. 1290543-63-3 ("Nirogacestat"). Substance Detail. Retrieved from SciFinder CAS Aug. 29, 2022. pp. 1-3. (Year: 2022).*

The United States Pharmacopeia, 23rd ed., 1843-4, USP-NF, United States (1995).
"Nirogacestat for Adults with Desmoid Tumor/Aggressive Fibromatosis (DT/AF) (DeFi)," ClinicalTrials.gov, https://clinicaltrials.gov/ct2/show/NCT03785964?term=nirogacestat&rank=1, accessed on Aug. 14, 2019, 10 pages.
"PF-03084014 hydrobromide," Millipore Sigma, SigmaAldrich.com, https://www.sigmaaldrich.com/catalog/product/sigma/pz0298?lang=en&region=US-, accessed on Aug. 14, 2019, 7 pages.
"A Study Evaluating PF-03084014 in Patients With Advanced Breast Cancer With or Without Notch Alterations," ClinicalTrials.gov, https://clinicaltrials.gov/ct2/show/NCT02299635?term=03084014&rank=1, accessed on Aug. 15, 2019, 8 pages.
"Gamma Secretase Inhibitor PF-03084014 in Treating Patients With AIDS-Associated Kaposi Sarcoma," ClinicalTrials.gov, https://clinicaltrials.gov/ct2/show/NCT02137564?term=030840 14&rank=2, accessed on Aug. 15, 2019, 9 pages.
"A Study of PF-03084014 in Japanese Patients With Advanced Solid Tumors," ClinicalTrials.gov, https://clinicaltrials.gov/ct2/show/NCT02462707?term=030840 1 4&rank:=3, accessed on Aug. 15, 2019, 5 pages.
"Phase II Trial of the Gamma-Secretase Inhibitor PF-03084014 in Adults With Desmoid Tumors/Aggressive Fibromatosis," ClinicalTrials.gov, https://clinicaltrials.gov/ct2/show/NCT01981551?term=030840 1 4&rank=4, accessed on Aug. 15, 2019, 10 pages.
"Biomarker Research Study for PF-03084014 in Chemoresistant Triple-negative Breast Cancer (RHEA)," ClinicalTrials.gov, https://clinicaltrials.gov/ct2/show/NCT0233853 1 ?term=03084014&rank=5, accessed on Aug. 15, 2019, 6 pages.
"A Study Evaluating the PF-03084014 in Combination With Docetaxel in Patients With Advanced Breast Cancer," ClinicalTrials.gov, https://clinicaltrials.gov/ct2/show/NCT01876251?term=03084014&rank=6, accessed on Aug. 15, 2019, 10 pages.
"Compassionate Use Protocol for PF-03084014 in Patients With Advanced Solid Tumor Malignancies," ClinicalTrials.gov, https://clinicaltrials.gov/ct2/showINCT02955446?term=030840 1 4&rank:=7, accessed on Aug. 15, 2019, 5 pages.
"Study of PF-03084014 in Combination With Gemcitabine and Nab-Paclitaxel in Patients With Metastatic Pancreatic Adenocarcinoma Not Previously Treated With Anticancer Therapies," ClinicalTrials.gov, https://clinicaltrials.gov/ct2/show/NCT02109445?term=03084014&rank:=8, accessed on Aug. 15, 2019, 12 pages.
"A Trial in Patients With Advanced Cancer and Leukemia," ClinicalTrials.gov, https://clinicaltrials.gov/ct2/show/NCT00878189?term=03084014&rank=9, accessed on Aug. 15, 2019, 16 pages.
Brodney, M.A., et al., "Design, Synthesis, and in vivo characterization of a novel series of tetralin amino imidazoles as y-secretase inhibitors: Discovery of PF-3084014," Bioorganic & Medicinal Chemistry Letters 21:2637-40, Elsevier, Netherlands (2011).
Kummar, S., et al., "Clinical Activity of the y-Secretase Inhibitor PF-03084014 in Adults With Desmoid Tumors (Aggressive Fibromatosis)," Journal of Clinical Oncology 35(14):1561-9, American Society of Clinical Oncology, United States (2017).

(Continued)

*Primary Examiner* — Leslie A. Royds Draper
(74) *Attorney, Agent, or Firm* — Sterne, Kessler, Goldstein & Fox P.L.L.C.

(57) ABSTRACT

The present disclosures are directed to chlorinated tetralin compounds and pharmaceutical compositions.

14 Claims, No Drawings

(56) References Cited

OTHER PUBLICATIONS

Shang, H., et al., "Targeting the Notch Pathway: A Potential Therapeutic Approach for Desmoid Tumors," Cancer 121(22):4088-96, John Wiley and Sons Inc., United States (2015).
Wei, P., et al., "Evaluation of Selective y-Secretase Inhibitor PF-03084014 for Its Antitumor Efficacy and Gastrointestinal Safety to Guide Optimal Clinical Trial Design," Molecular Cancer Therapeutics 9(6):1618-28, American Association for Cancer Research, United States (2010).
Aurora Building Blocks 4, Accession No. 1921685693 Chemcats, CAS Registry No. 1962925-29-6, Feb. 27, 2020, 2 pages.
International Search Report and Written Opinion for International Application No. PCT/US2019/045948, European Patent Office, Netherlands, dated Jul. 6, 2020, 10 pages.
Berge, S. M., et al., "Pharmaceutical Salts," Journal of Pharmaceutical Sciences 66(1):1-19, Elsevier, United States (Jan. 1977).
Takahashi, T., et al., "Safety and efficacy of gamma-secretase inhibitor nirogacestat (PF-03084014) in desmoid tumor: Report of four pediatric/young adult cases," Pediatr Blood Cancer 67:e28636, Wiley, United States (Jul. 2020).
Silverman, R.B., "The Organic Chemistry of Drug Design and Drug Action (Second Edition)," pp. 29-32, Elsevier Academic Press, United States (2004).

* cited by examiner

CHLORINATED TETRALIN COMPOUNDS AND PHARMACEUTICAL COMPOSITIONS

REFERENCE TO RELATED APPLICATIONS

The present application is a continuation of U.S. Non Provisional application Ser. No. 17/860,682, filed Jul. 8, 2022 and claims priority benefit to U.S. Provisional Application No. 63/241,844, filed Sep. 8, 2021, U.S. Provisional Application No. 63/263,635, filed Nov. 5, 2021, and U.S. Provisional Application No. 63/365,125, filed May 20, 2022 which is each hereby incorporated by reference in its entirety.

FIELD OF THE DISCLOSURE

The present disclosure relates to chlorinated tetralin compounds and pharmaceutical compositions comprising them. The pharmaceutical compositions can comprise a chlorinated tetralin compound and a gamma-secretase inhibitor, such as nirogacestat.

BACKGROUND

Chlorinated tetralin compounds can be generated during a synthetic process of (S)-2-((S)-6,8-difluoro-1,2,3,4-tetrahydronaphthalen-2-ylamino)-N-(1-(2-methyl-1-(neopentylamino)propan-2-yl)-1H-imidazol-4-yl)pentanamide ("nirogacestat"). Nirogacestat exhibits promising activity for the treatment of tumors or cancer, such as desmoid tumors, multiple myeloma, a cancer having a mutation in a Notch pathway gene, adenoid cystic carcinoma, and T-cell acute lymphoblastic leukemia.

BRIEF SUMMARY OF THE DISCLOSURE

The disclosure relates to a compound of Formula I:

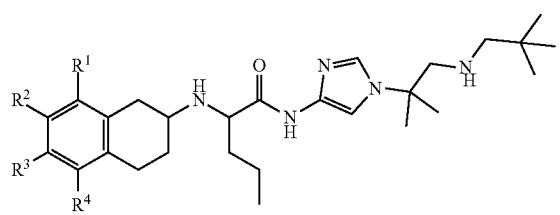

(I)

or a pharmaceutically acceptable salt thereof, wherein $R^1$, $R^2$, $R^3$ and $R^4$ are individually hydrogen or halogen, and at least one of $R^1$, $R^2$, $R^3$ and $R^4$ is chloro.

In some aspects, the compound of Formula I is selected from the group consisting of (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide, (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide, and (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide.

In some aspects, the compound of Formula I is that of Formula IA

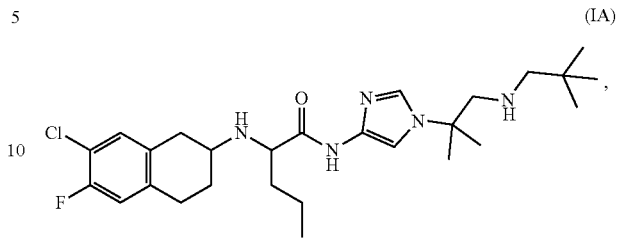

(IA)

or a pharmaceutically acceptable salt thereof.

In some aspects, the compound of Formula I is that of Formula IB

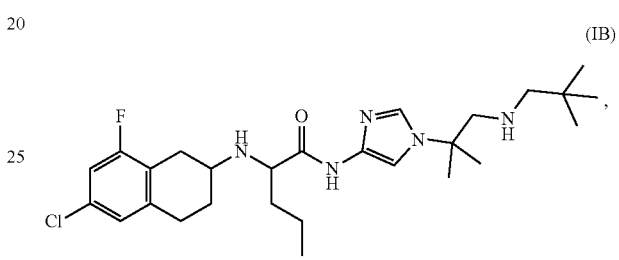

(IB)

or a pharmaceutically acceptable salt thereof.

In some aspects, the compound of Formula I is that of Formula IC

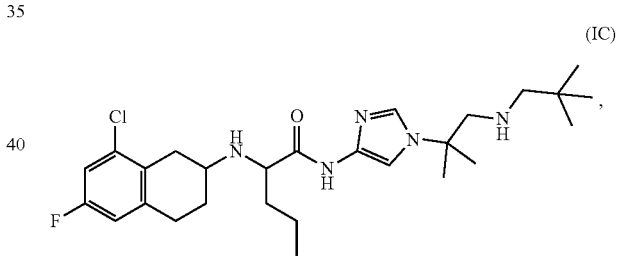

(IC)

or a pharmaceutically acceptable salt thereof.

The disclosure further relates to a pharmaceutical composition comprising a compound of Formula I:

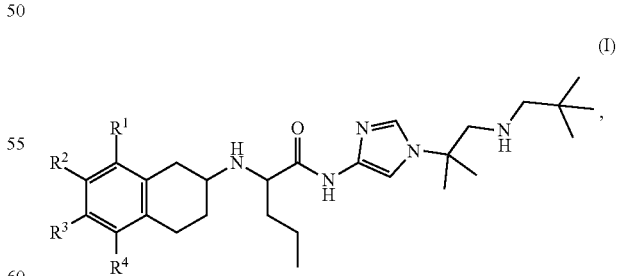

(I)

or a pharmaceutically acceptable salt thereof, wherein $R^1$, $R^2$, $R^3$ and $R^4$ are individually hydrogen or halogen, and at least one of $R^1$, $R^2$, $R^3$ and $R^4$ is chloro.

In some aspects, the pharmaceutical composition comprises a compound of Formula I selected from the group consisting of (S)-2-(((S)-7-chloro-6-fluoro-1,2,3,4-tetrahydronaphthalen-2-yl)amino)-N-(1-(2-methyl-1-(neopenty-lamino)propan-2-yl)-1H-imidazol-4-yl)pentanamide dihydrobromide, (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl) pentanamide dihydrobromide, and (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl) pentanamide dihydrobromide.

In some aspects, the compound of Formula I or pharmaceutically acceptable salt thereof in the pharmaceutical composition is present in an amount of about 1 µg to about 500 µg. In some aspects, the compound of Formula I or pharmaceutically acceptable salt thereof in the pharmaceutical composition is present in an amount of about 5 µg to about 500 µg. In some aspects, the compound of Formula I or pharmaceutically acceptable salt thereof in the pharmaceutical composition is present in an amount of about 10 µg to about 250 µg. In some aspects, the compound of Formula I or pharmaceutically acceptable salt thereof in the pharmaceutical composition is present in an amount of about 10 µg to about 100 µg. In some aspects, the compound of Formula I or pharmaceutically acceptable salt thereof in the pharmaceutical composition is present in an amount of about 10 µg to about 50 µg. In some aspects, the compound of Formula I or pharmaceutically acceptable salt thereof in the pharmaceutical composition is present in an amount of about 12.5 µg to about 50 µg. In some aspects, the pharmaceutical composition comprising a compound of Formula I or pharmaceutically acceptable salt thereof further comprises a gamma-secretase inhibitor selected from the group consisting of nirogacestat, or a pharmaceutically acceptable salt thereof, crenigacestat, or a pharmaceutically acceptable salt thereof, AL101, or a pharmaceutically acceptable salt thereof, AL102, or a pharmaceutically acceptable salt thereof, semagacestat, or a pharmaceutically acceptable salt thereof, avagacestat, and ianabecestat, or a pharmaceutically acceptable salt thereof. In some aspects, the pharmaceutical composition comprising a compound of Formula I or pharmaceutically acceptable salt thereof further comprises nirogacestat, or a pharmaceutically acceptable salt thereof.

The disclosure further relates to a pharmaceutical composition comprising a compound of Formula I which is that of Formula IA

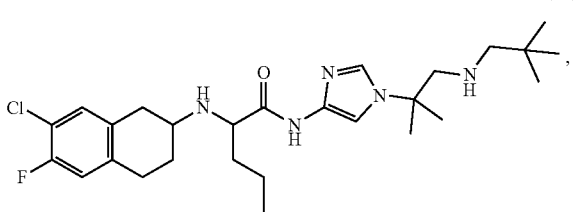

(IA)

or a pharmaceutically acceptable salt thereof. In some aspects, the compound of Formula IA or pharmaceutically acceptable salt thereof in the pharmaceutical composition is present in an amount of about 1 µg to about 500 µg. In some aspects, the compound of Formula IA or pharmaceutically acceptable salt thereof in the pharmaceutical composition is present in an amount of about 5 µg to about 500 µg. In some aspects, the compound of Formula IA or pharmaceutically acceptable salt thereof in the pharmaceutical composition is present in an amount of about 10 µg to about 250 µg. In some aspects, the compound of Formula IA or pharmaceutically acceptable salt thereof in the pharmaceutical composition is present in an amount of about 10 µg to about 100 µg. In some aspects, the compound of Formula IA or pharmaceutically acceptable salt thereof in the pharmaceutical composition is present in an amount of about 10 µg to about 50 µg. In some aspects, the compound of Formula IA or pharmaceutically acceptable salt thereof in the pharmaceutical composition is present in an amount of about 12.5 µg to about 50 µg. In some aspects, the pharmaceutical composition comprising a compound of Formula IA or pharmaceutically acceptable salt thereof further comprises a gamma-secretase inhibitor selected from the group consisting of nirogacestat, or a pharmaceutically acceptable salt thereof, crenigacestat, or a pharmaceutically acceptable salt thereof, AL101, or a pharmaceutically acceptable salt thereof, AL102, or a pharmaceutically acceptable salt thereof, semagacestat, or a pharmaceutically acceptable salt thereof, avagacestat, or a pharmaceutically acceptable salt thereof, and ianabecestat or a pharmaceutically acceptable salt thereof. In some aspects, the pharmaceutical composition comprising a compound of Formula IA or pharmaceutically acceptable salt thereof further comprises nirogacestat, or a pharmaceutically acceptable salt thereof.

The disclosure further relates to a pharmaceutical composition comprising a compound of Formula I which is that of Formula IB

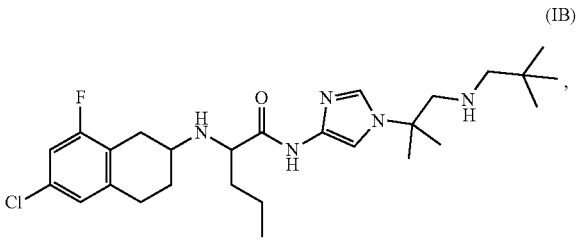

(IB)

or a pharmaceutically acceptable salt thereof. In some aspects, the compound of Formula IB or pharmaceutically acceptable salt thereof in the pharmaceutical composition is present in an amount of about 1 µg to about 500 µg. In some aspects, the compound of Formula IB or pharmaceutically acceptable salt thereof in the pharmaceutical composition is present in an amount of about 5 µg to about 500 µg. In some aspects, the compound of Formula IB or pharmaceutically acceptable salt thereof in the pharmaceutical composition is present in an amount of about 10 µg to about 250 µg. In some aspects, the compound of Formula IB or pharmaceutically acceptable salt thereof in the pharmaceutical composition is present in an amount of about 10 µg to about 100 µg. In some aspects, the compound of Formula IB or pharmaceutically acceptable salt thereof in the pharmaceutical composition is present in an amount of about 10 µg to about 50 µg. In some aspects, the compound of Formula IB or pharmaceutically acceptable salt thereof in the pharmaceutical composition is present in an amount of about 12.5 µg to about 50 µg. In some aspects, the pharmaceutical composition comprising a compound of Formula IB or pharmaceutically acceptable salt thereof further comprises a gamma-secretase inhibitor selected from the group consisting of nirogacestat, or a pharmaceutically acceptable salt thereof, crenigacestat, or a pharmaceutically acceptable salt thereof, AL101, or a pharmaceutically acceptable salt thereof, AL102, or a pharmaceutically acceptable salt thereof, semagacestat, or a pharmaceutically acceptable salt thereof, avagacestat, or a pharmaceutically acceptable salt thereof, and ianabecestat, or a pharmaceutically acceptable salt thereof. In some aspects, the pharmaceutical composition comprising a compound of Formula IB or pharmaceutically acceptable salt thereof further comprises nirogacestat, or a pharmaceutically acceptable salt thereof.

The disclosure further relates to a pharmaceutical composition comprising a compound of Formula I which is a compound of Formula IC

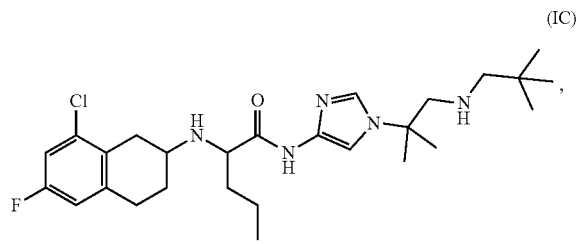

(IC)

or a pharmaceutically acceptable salt thereof. In some aspects, the compound of Formula IC in the pharmaceutical composition is present in an amount of about 1 µg to about 500 µg. In some aspects, the compound of Formula IC in the pharmaceutical composition is present in an amount of about 5 µg to about 500 µg. In some aspects, the compound of Formula IC in the pharmaceutical composition is present in an amount of about 10 µg to about 250 µg. In some aspects, the compound of Formula IC in the pharmaceutical composition is present in an amount of about 10 µg to about 100 µg. In some aspects, the compound of Formula IC in the pharmaceutical composition is present in an amount of about 10 µg to about 50 µg. In some aspects, the compound of Formula IC in the pharmaceutical composition is present in an amount of about 12.5 µg to about 50 µg. In some aspects, the pharmaceutical composition comprising a compound of Formula IC further comprises a gamma-secretase inhibitor selected from the group consisting of nirogacestat, or a pharmaceutically acceptable salt thereof, crenigacestat, or a pharmaceutically acceptable salt thereof, AL101, or a pharmaceutically acceptable salt thereof, AL102, or a pharmaceutically acceptable salt thereof, semagacestat, or a pharmaceutically acceptable salt thereof, avagacestat, or a pharmaceutically acceptable salt thereof, and ianabecestat, or a pharmaceutically acceptable salt thereof. In some aspects, the pharmaceutical composition comprising a compound of Formula IC further comprises nirogacestat, or a pharmaceutically acceptable salt thereof.

In some aspects, the pharmaceutical composition comprising a compound of Formula I, Formula IA, Formula IB, or Formula IC further comprises a pharmaceutically acceptable carrier. In some aspects, the pharmaceutical composition comprising a compound of Formula I, Formula IA, Formula IB, or Formula IC is for oral administration. In some aspects, the pharmaceutical composition comprising a compound of Formula I, Formula IA, Formula IB, or Formula IC is a tablet.

The present disclosure further relates to methods of treating tumors comprising administering to a subject in need of such treatment a pharmaceutical composition comprising a compound of Formula I, Formula IA, Formula IB, or Formula IC. In some aspects, the tumors are desmoid tumors.

The present disclosure further relates to methods of treating cancer comprising administering to a subject in need of such treatment, a pharmaceutical composition comprising a compound of Formula I, Formula IA, Formula IB, or Formula IC. In some aspects, the cancer is selected from the group consisting of multiple myeloma, a cancer having a mutation in a Notch pathway gene, adenoid cystic carcinoma, and T-cell acute lymphoblastic leukemia.

DETAILED DESCRIPTION

I. Definitions and Abbreviations

As used above, and throughout the description, the following terms, unless otherwise indicated, shall be understood to have the following meanings.

Unless stated otherwise, the terms "a" and "an" and "the" and similar references used in the context of describing a particular aspect of the application (especially in the context of claims) can be construed to cover both the singular and the plural. The recitation of ranges of values herein is merely intended to serve as a shorthand process of referring individually to each separate value falling within the range. Unless otherwise indicated herein, each individual value is incorporated into the specification as if it were individually recited herein.

The term "pharmaceutical composition," as used herein, represents a composition containing a compound described herein formulated with a pharmaceutically acceptable excipient, and can be manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); for intrathecal injection; for intracerebroventricular injections; for intraparenchymal injection; or in any other pharmaceutically acceptable formulation.

The terms "pharmaceutically acceptable carrier," "pharmaceutically acceptable excipient," "physiologically acceptable carrier," or "physiologically acceptable excipient" refer to a pharmaceutically acceptable material, composition, or vehicle, such as a liquid or solid filler, diluent, excipient, solvent, or encapsulating material. In one aspect, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See *Remington: The Science and Practice of Pharmacy,* 21$^{st}$ Edition, Lippincott Williams & Wilkins Philadelphia, Pa., 2005; *Handbook of Pharmaceutical Excipients,* 5$^{th}$ Edition, Rowe et al., Eds., The Pharmaceutical Press and the American Pharmaceutical Association: 2005; and *Handbook of Pharmaceutical Additives,* 3$^{rd}$ Edition, Ash and Ash Eds., Gower Publishing Company: 2007; Pharmaceutical Preformulation and Formulation, Gibson Ed., CRC Press LLC: Boca Raton, Fla., 2004 (incorporated herein by reference). Excipients can include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

The term "pharmaceutically-acceptable salts" refers to the relatively non-toxic, inorganic and organic acid addition salts of Compound A or Compound B. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In certain aspects, the compounds of the present invention may contain one or more acidic functional groups and, thus, are capable of forming pharmaceutically acceptable salts with pharmaceutically acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, e.g., Berge et al., supra).

The terms "about" or "approximately" means within a range of an acceptable error for a particular value as determined by one of ordinary skill in the art, which depends in part on how the value is measured or determined. In certain aspects, the term "about" or "approximately" means within 1, 2, 3, or 4 standard deviations. In some aspects, the term "about" or "approximately" means a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

As used herein, the term "administration" refers to the administration of a composition (e.g., a compound or a preparation that includes a compound as described herein) to a subject or system. Administration to an animal subject (e.g., to a human) can be by any appropriate route, such as one described herein.

The terms "comprise," "comprises," and "comprising" are used on the basis and clear understanding that they are to be interpreted inclusively, rather than exclusively.

II. Chlorinated Tetralin Compounds

The disclosure relates to a compound of Formula I:

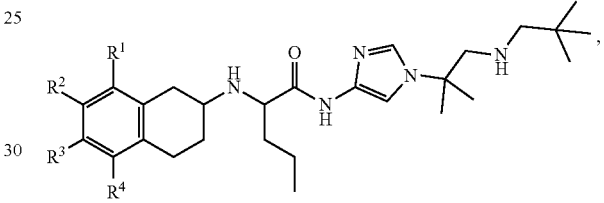

or a pharmaceutically acceptable salt thereof, wherein $R^1$, $R^2$, $R^3$ and $R^4$ are individually hydrogen or halogen, and at least one of $R^1$, $R^2$, $R^3$ and $R^4$ is chloro. In some aspects, $R^1$ is chloro, and $R^2$, $R^3$ and $R^4$ are individually hydrogen or halogen. In some aspects, $R^2$ is chloro, and $R^1$, $R^3$ and $R^4$ are individually hydrogen or halogen. In some aspects, $R^3$ is chloro, and $R^1$, $R^2$ and $R^4$ are individually hydrogen or halogen. In some aspects, $R^4$ is chloro, and $R^1$, $R^2$ and $R^3$ are individually hydrogen or halogen. In some aspects, $R^1$ and $R^2$ are individually chloro, and $R^3$ and $R^4$ are individually hydrogen or halogen. In some aspects, $R^1$ and $R^3$ are individually chloro, and $R^2$ and $R^4$ are individually hydrogen or halogen. In some aspects, $R^1$ and $R^4$ are chloro, and $R^2$ and $R^3$ are hydrogen or halogen. In some aspects, $R^2$ and $R^3$ are chloro, and $R^1$ and $R^4$ are hydrogen or halogen. In some aspects, $R^2$ and $R^4$ are individually chloro, and $R^1$ and $R^3$ are individually hydrogen or halogen. In some aspects, $R^3$ and $R^4$ are individually chloro, and $R^1$ and $R^2$ are individually hydrogen or halogen. In some aspects, $R^1$, $R^2$ and $R^3$ are individually chloro, and $R^4$ is hydrogen or halogen. In some aspects, $R^1$, $R^2$ and $R^4$ are individually chloro, and $R^3$ is hydrogen or halogen. In some aspects, $R^1$, $R^3$ and $R^4$ are individually chloro, and $R^2$ is hydrogen or halogen. In some aspects, $R^2$, $R^3$ and $R^4$ are individually chloro, and $R^1$ is hydrogen or halogen. In some aspects, $R^1$, $R^2$, $R^3$ and $R^4$ are individually chloro.

In some aspects, the compound of Formula I is selected from the group consisting of (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide, (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide, and (S)-2-(((S)-8-chloro-6- fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide.

In some aspects, the compound of Formula I is (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide.

In some aspects, the compound of Formula I is (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide.

In some aspects, the compound of Formula I is (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide.

In some aspects, the compound of Formula I is that of Formula IA

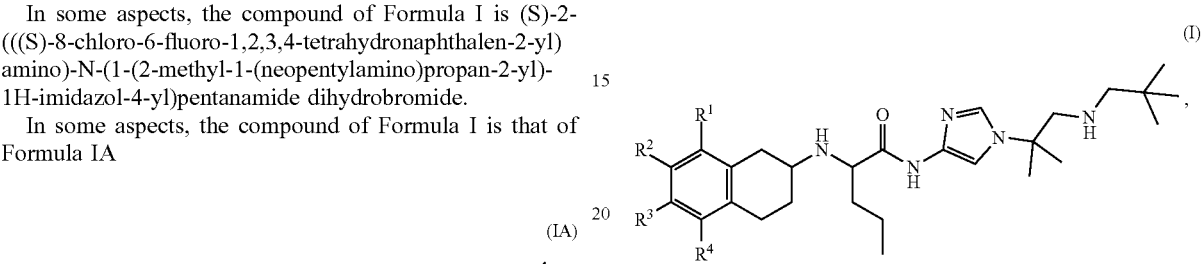

(IA)

or a pharmaceutically acceptable salt thereof.

In some aspects, the compound of Formula I is that of Formula IB

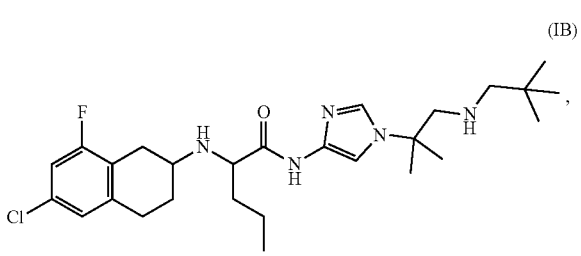

(IB)

or a pharmaceutically acceptable salt thereof.

In some aspects, the compound of Formula I is that of Formula IC

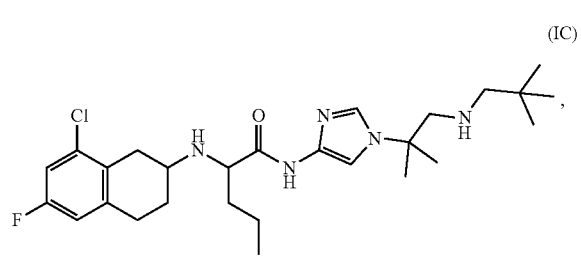

(IC)

or a pharmaceutically acceptable salt thereof.

In some aspects, the compound of Formula I, Formula IA, Formula IB, and Formula IC is in the free base form.

In some aspects, the compound of Formula I, Formula IA, Formula IB, and Formula IC is in a pharmaceutically acceptable salt form. In some aspects, the pharmaceutically acceptable salt form of the compound of Formula I, Formula IA, Formula IB, and Formula IC is a hydrobromide salt form. In some aspects, the pharmaceutically acceptable salt form of the compound of Formula I, Formula IA, Formula IB, and Formula IC is a dihydrobromide salt form.

III. Pharmaceutical Compositions

The disclosure further relates to a pharmaceutical composition comprising a compound of Formula I:

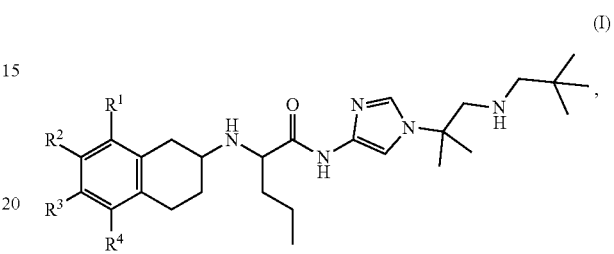

(I)

or a pharmaceutically acceptable salt thereof, wherein $R^1$, $R^2$, $R^3$ and $R^4$ are individually hydrogen or halogen, and at least one of $R^1$, $R^2$, $R^3$ and $R^4$ is chloro. In some aspects, the pharmaceutical composition comprises a compound of Formula I or a pharmaceutically acceptable salt thereof, wherein $R^1$ is chloro, and $R^2$, $R^3$ and $R^4$ are individually hydrogen or halogen. In some aspects, the pharmaceutical composition comprises a compound of Formula I or a pharmaceutically acceptable salt thereof, wherein $R^2$ is chloro, and $R^1$, $R^3$ and $R^4$ are individually hydrogen or halogen. In some aspects, the pharmaceutical composition comprises a compound of Formula I or a pharmaceutically acceptable salt thereof, wherein $R^3$ is chloro, and $R^1$, $R^2$ and $R^4$ are individually hydrogen or halogen. In some aspects, the pharmaceutical composition comprises a compound of Formula I or a pharmaceutically acceptable salt thereof, wherein $R^4$ is chloro, and $R^1$, $R^2$ and $R^3$ are individually hydrogen or halogen. In some aspects, the pharmaceutical composition comprises a compound of Formula I or a pharmaceutically acceptable salt thereof, wherein $R^1$ and $R^2$ are chloro, and $R^3$ and $R^4$ are individually hydrogen or halogen. In some aspects, the pharmaceutical composition comprises a compound of Formula I or a pharmaceutically acceptable salt thereof, wherein $R^1$ and $R^3$ are individually chloro, and $R^2$ and $R^4$ are individually hydrogen or halogen. In some aspects, the pharmaceutical composition comprises a compound of Formula I or a pharmaceutically acceptable salt thereof, wherein $R^1$ and $R^4$ are individually chloro, and $R^2$ and $R^3$ are individually hydrogen or halogen. In some aspects, the pharmaceutical composition comprises a compound of Formula I or a pharmaceutically acceptable salt thereof, wherein $R^2$ and $R^3$ are individually chloro, and $R^1$ and $R^4$ are individually hydrogen or halogen. In some aspects, the pharmaceutical composition comprises a compound of Formula I or a pharmaceutically acceptable salt thereof, wherein $R^2$ and $R^4$ are individually chloro, and $R^1$ and $R^3$ are individually hydrogen or halogen. In some aspects, the pharmaceutical composition comprises a compound of Formula I or a pharmaceutically acceptable salt thereof, wherein $R^3$ and $R^4$ are individually chloro, and $R^1$ and $R^2$ are individually hydrogen or halogen. In some aspects, the pharmaceutical composition comprises a compound of Formula I or a pharmaceutically acceptable salt thereof, wherein $R^1$, $R^2$ and $R^3$ are individually chloro, and $R^4$ is hydrogen or halogen. In some aspects, the pharmaceutical composition comprises a compound of Formula I or a pharmaceutically acceptable salt thereof, wherein $R^1$, $R^2$ and $R^4$ are individually chloro, and $R^3$ is hydrogen or halogen. In some aspects, the pharmaceutical composition comprises a compound of Formula I or a pharmaceutically acceptable salt thereof, wherein $R^1$, $R^3$ and $R^4$ are individually chloro, and $R^2$ is hydrogen or halogen. In some aspects, the pharmaceutical composition comprises a compound of Formula I or a pharmaceutically acceptable salt thereof, wherein $R^2$, $R^3$ and $R^4$ are individually chloro, and R' is hydrogen or halogen. In some aspects, the pharmaceutical composition comprises a compound of Formula I or a pharmaceutically acceptable salt thereof, wherein $R^1$, $R^2$, $R^3$ and $R^4$ are individually chloro.

In some aspects, the compound of Formula I or pharmaceutically acceptable salt thereof in the pharmaceutical composition is present in an amount of about 1 μg to about 500 μg. In some aspects, the compound of Formula I or pharmaceutically acceptable salt thereof in the pharmaceutical composition is present in an amount of about 2 μg to about 500 μg. In some aspects, the compound of Formula I or pharmaceutically acceptable salt thereof in the pharmaceutical composition is present in an amount of about 3 μg to about 500 μg. In some aspects, the compound of Formula I or pharmaceutically acceptable salt thereof in the pharmaceutical composition is present in an amount of about 4 μg to about 500 μg. In some aspects, the compound of Formula I or pharmaceutically acceptable salt thereof in the pharmaceutical composition is present in an amount of about 5 μg to about 500 μg. In some aspects, the compound of Formula I or pharmaceutically acceptable salt thereof in the pharmaceutical composition is present in an amount of about 6 μg to about 475 μg. In some aspects, the compound of Formula I or pharmaceutically acceptable salt thereof in the pharmaceutical composition is present in an amount of about 6 μg to about 450 μg. In some aspects, the compound of Formula I or pharmaceutically acceptable salt thereof in the pharmaceutical composition is present in an amount of about 7 μg to about 425 μg. In some aspects, the compound of Formula I or pharmaceutically acceptable salt thereof in the pharmaceutical composition is present in an amount of about 7 μg to about 400 μg. In some aspects, the compound of Formula I or pharmaceutically acceptable salt thereof in the pharmaceutical composition is present in an amount of about 8 μg to about 375 μg. In some aspects, the compound of Formula I or pharmaceutically acceptable salt thereof in the pharmaceutical composition is present in an amount of about 8 μg to about 350 μg. In some aspects, the compound of Formula I or pharmaceutically acceptable salt thereof in the pharmaceutical composition is present in an amount of about 9 μg to about 325 μg. In some aspects, the compound of Formula I or pharmaceutically acceptable salt thereof in the pharmaceutical composition is present in an amount of about 9 μg to about 300 μg. In some aspects, the compound of Formula I or pharmaceutically acceptable salt thereof in the pharmaceutical composition is present in an amount of about 10 μg to about 275 μg. In some aspects, the compound of Formula I or pharmaceutically acceptable salt thereof in the pharmaceutical composition is present in an amount of about 10 μg to about 250 μg. In some aspects, the compound of Formula I or pharmaceutically acceptable salt thereof in the pharmaceutical composition is present in an amount of about 10 μg to about 225 μg. In some aspects, the compound of Formula I or pharmaceutically acceptable salt thereof in the pharmaceutical composition is present in an amount of about 10 μg to about 200 μg. In some aspects, the compound of Formula I or pharmaceutically acceptable salt thereof in the pharmaceutical composition is present in an amount of about 10 μg to about 175 μg. In some aspects, the compound of Formula I or pharmaceutically acceptable salt thereof in the pharmaceutical composition is present in an amount of about 10 μg to about 150 μg. In some aspects, the compound of Formula I or pharmaceutically acceptable salt thereof in the pharmaceutical composition is present in an amount of about 10 μg to about 125 μg. In some aspects, the compound of Formula I or pharmaceutically acceptable salt thereof in the pharmaceutical composition is present in an amount of about 10 μg to about 100 μg. In some aspects, the compound of Formula I or pharmaceutically acceptable salt thereof in the pharmaceutical composition is present in an amount of about 10 μg to about 90 μg. In some aspects, the compound of Formula I or pharmaceutically acceptable salt thereof in the pharmaceutical composition is present in an amount of about 10 μg to about 80 μg. In some aspects, the compound of Formula I or pharmaceutically acceptable salt thereof in the pharmaceutical composition is present in an amount of about 10 μg to about 70 μg. In some aspects, the compound of Formula I or pharmaceutically acceptable salt thereof in the pharmaceutical composition is present in an amount of about 10 μg to about 60 μg. In some aspects, the compound of Formula I or pharmaceutically acceptable salt thereof in the pharmaceutical composition is present in an amount of about 10 μg to about 50 μg. In some aspects, the compound of Formula I or pharmaceutically acceptable salt thereof in the pharmaceutical composition is present in an amount of about 11 μg to about 50 μg. In some aspects, the compound of Formula I or pharmaceutically acceptable salt thereof in the pharmaceutical composition is present in an amount of about 12 μg to about 50 μg. In some aspects, the compound of Formula I or pharmaceutically acceptable salt thereof in the pharmaceutical composition is present in an amount of about 12.5 μg to about 50 μg.

In some aspects, the pharmaceutical composition comprising a compound of Formula I or pharmaceutically acceptable salt thereof further comprises a gamma-secretase inhibitor selected from the group consisting of nirogacestat, or a pharmaceutically acceptable salt thereof, crenigacestat, or a pharmaceutically acceptable salt thereof, AL101, or a pharmaceutically acceptable salt thereof, AL102, or a pharmaceutically acceptable salt thereof, semagacestat, or a pharmaceutically acceptable salt thereof, avagacestat, or a pharmaceutically acceptable salt thereof, and ianabecestat, or a pharmaceutically acceptable salt thereof. In some aspects, the pharmaceutical composition comprising a compound of Formula I or pharmaceutically acceptable salt thereof further comprises nirogacestat, or a pharmaceutically acceptable salt thereof. In some aspects, the pharmaceutical composition comprising a compound of Formula I or pharmaceutically acceptable salt thereof further comprises crenigacestat, or a pharmaceutically acceptable salt thereof. In some aspects, the pharmaceutical composition comprising a compound of Formula I or pharmaceutically acceptable salt thereof further comprises AL101, or a pharmaceutically acceptable salt thereof. In some aspects, the pharmaceutical composition comprising a compound of Formula I or pharmaceutically acceptable salt thereof further comprises AL102, or a pharmaceutically acceptable salt thereof. In some aspects, the pharmaceutical composition comprising a compound of Formula I or pharmaceutically acceptable salt thereof further comprises semagacestat, or a pharmaceutically acceptable salt thereof. In some aspects, the pharmaceutical composition comprising a compound of Formula I or pharmaceutically acceptable salt thereof further comprises avagacestat, or a pharmaceutically acceptable salt thereof. In some aspects, the pharmaceutical composition comprising a compound of Formula I or pharmaceutically acceptable salt thereof further comprises ianabecestat, or a pharmaceutically acceptable salt thereof. In some aspects, the pharmaceutical composition comprising a compound of Formula I or pharmaceutically acceptable salt thereof further comprises nirogacestat hydrobromide. In some aspects, the pharmaceutical composition comprising a compound of Formula I or pharmaceutically acceptable salt thereof further comprises nirogacestat dihydrobromide.

In some aspects, the pharmaceutical composition comprises a compound of Formula I or pharmaceutically acceptable salt thereof selected from the group consisting of (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide, (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide, and (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide.

In some aspects, the pharmaceutical composition comprises a compound of Formula I or pharmaceutically acceptable salt thereof that is (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 1 µg to about 500 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 2 µg to about 500 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 3 µg to about 500 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 4 µg to about 500 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 5 µg to about 500 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 6 µg to about 475 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 6 µg to about 450 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 7 µg to about 425 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 7 µg to about 400 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 8 µg to about 375 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 8 µg to about 350 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 9 µg to about 325 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 9 µg to about 300 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 275 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 250 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 225 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 200 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 175 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 150 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 125 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 100 µg. In some aspects, the (S)-2-(((S)-7-chloro-6-fluoro- 1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 90 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 80 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 70 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 60 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 50 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 11 µg to about 50 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 12 µg to about 50 µg. In some aspects, the (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 12.5 µg to about 50 µg.

In some aspects, the pharmaceutical composition comprising (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises a gamma-secretase inhibitor selected from the group consisting of nirogacestat, or a pharmaceutically acceptable salt thereof, crenigacestat, or a pharmaceutically acceptable salt thereof, AL101, or a pharmaceutically acceptable salt thereof, AL102, or a pharmaceutically acceptable salt thereof, semagacestat, or a pharmaceutically acceptable salt thereof, avagacestat, or a pharmaceutically acceptable salt thereof, and ianabecestat, or a pharmaceutically acceptable salt thereof. In some aspects, the pharmaceutical composition comprising (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises nirogacestat, or a pharmaceutically acceptable salt thereof. In some aspects, the pharmaceutical composition comprising (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises crenigacestat, or a pharmaceutically acceptable salt thereof. In some aspects, the pharmaceutical composition comprising (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises AL101, or a pharmaceutically acceptable salt thereof. In some aspects, the pharmaceutical composition comprising (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises AL102, or a pharmaceutically acceptable salt thereof. In some aspects, the pharmaceutical composition comprising (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises semagacestat. In some aspects, the pharmaceutical composition comprising (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises avagacestat, or a pharmaceutically acceptable salt thereof. In some aspects, the pharmaceutical composition comprising (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises ianabecestat, or a pharmaceutically acceptable salt thereof. In some aspects, the pharmaceutical composition comprising (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises nirogacestat hydrobromide. In some aspects, the pharmaceutical composition comprising (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises nirogacestat dihydrobromide.

In some aspects, the pharmaceutical composition comprises a compound of Formula I that is (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 1 µg to about 500 µg. In some aspects, (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 2 µg to about 500 µg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 3 µg to about 500 µg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 4 µg to about 500 µg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 5 µg to about 500 µg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 6 µg to about 475 µg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 6 μg to about 450 μg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 7 μg to about 425 μg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 7 μg to about 400 μg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 8 μg to about 375 μg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 8 μg to about 350 μg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 9 μg to about 325 μg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 9 μg to about 300 μg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 μg to about 275 μg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 μg to about 250 μg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 μg to about 225 μg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 μg to about 200 μg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 μg to about 175 μg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 μg to about 150 μg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 μg to about 125 μg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 μg to about 100 μg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 μg to about 90 μg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 μg to about 80 μg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 μg to about 70 μg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 μg to about 60 μg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 μg to about 50 μg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 11 μg to about 50 μg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 12 μg to about 50 μg. In some aspects, the (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 12.5 μg to about 50 μg.

In some aspects, the pharmaceutical composition comprising (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises a gamma-secretase inhibitor selected from the group consisting of nirogacestat, crenigacestat, AL101, AL102, semagacestat, avagacestat, and ianabecestat. In some aspects, the pharmaceutical composition comprising (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises nirogacestat, or a pharmaceutically acceptable salt thereof. In some aspects, the pharmaceutical composition comprising (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises crenigacestat, or pharmaceutically acceptable salt thereof. In some aspects, the pharmaceutical composition comprising (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises AL101, or pharmaceutically acceptable salt thereof. In some aspects, the pharmaceutical composition comprising (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises AL102, or pharmaceutically acceptable salt thereof. In some aspects, the pharmaceutical composition comprising (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises semagacestat, or pharmaceutically acceptable salt thereof. In some aspects, the pharmaceutical composition comprising (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises avagacestat. In some aspects, the pharmaceutical composition comprising (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises ianabecestat, or pharmaceutically acceptable salt thereof. In some aspects, the pharmaceutical composition comprising (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises nirogacestat hydrobromide. In some aspects, the pharmaceutical composition comprising (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises nirogacestat dihydrobromide.

In some aspects, the pharmaceutical composition comprises a compound of Formula I that is (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 1 µg to about 500 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 2 µg to about 500 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 3 µg to about 500 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 4 µg to about 500 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 5 µg to about 500 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 6 µg to about 475 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 6 µg to about 450 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 7 µg to about 425 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 7 µg to about 400 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 8 µg to about 375 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 8 µg to about 350 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 9 µg to about 325 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 9 µg to about 300 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 275 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 250 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 225 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 200 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 175 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 150 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 125 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 100 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 90 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 80 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 70 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 60 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 10 µg to about 50 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 11 µg to about 50 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 12 µg to about 50 µg. In some aspects, the (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide in the pharmaceutical composition is present in an amount of about 12.5 µg to about 50 µg.

In some aspects, the pharmaceutical composition comprising (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises a gamma-secretase inhibitor selected from the group consisting of nirogacestat, or a pharmaceutically acceptable salt thereof, crenigacestat, or a pharmaceutically acceptable salt thereof, AL101, or a pharmaceutically acceptable salt thereof, AL102, or a pharmaceutically acceptable salt thereof, semagacestat, or a pharmaceutically acceptable salt thereof, avagacestat, and ianabecestat, or a pharmaceutically acceptable salt thereof. In some aspects, the pharmaceutical composition comprising (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises nirogacestat, or a pharmaceutically acceptable salt thereof. In some aspects, the pharmaceutical composition comprising (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises crenigacestat, or pharmaceutically acceptable salt thereof. In some aspects, the pharmaceutical composition comprising (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises AL101, or pharmaceutically acceptable salt thereof. In some aspects, the pharmaceutical composition comprising (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises AL102, or pharmaceutically acceptable salt thereof. In some aspects, the pharmaceutical composition comprising (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises semagacestat, or pharmaceutically acceptable salt thereof. In some aspects, the pharmaceutical composition comprising (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises avagacestat, or pharmaceutically acceptable salt thereof. In some aspects, the pharmaceutical composition comprising (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises ianabecestat, or pharmaceutically acceptable salt thereof. In some aspects, the pharmaceutical composition comprising (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises nirogacestat hydrobromide. In some aspects, the pharmaceutical composition comprising (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide further comprises nirogacestat dihydrobromide The disclosure further relates to a pharmaceutical composition comprising a compound of Formula I which is the compound of Formula IA (IA)

or a pharmaceutically acceptable salt thereof. In some aspects, the compound of Formula IA or pharmaceutically acceptable salt thereof in the pharmaceutical composition is present in an amount of about 1 µg to about 500 µg. In some aspects, the compound of Formula IA or pharmaceutically acceptable salt thereof in the pharmaceutical composition is present in an amount of about 2 µg to about 500 µg. In some aspects, the compound of Formula IA or pharmaceutically acceptable salt thereof in the pharmaceutical composition is present in an amount of about 3 µg to about 500 µg. In some aspects, the compound of Formula IA or pharmaceutically acceptable salt thereof in the pharmaceutical composition is present in an amount of about 4 µg to about 500 µg. In some aspects, the compound of Formula IA or pharmaceutically acceptable salt thereof in the pharmaceutical composition is present in an amount of about 5 µg to about 500 µg. In some aspects, the compound of Formula IA or pharmaceutically acceptable salt thereof in the pharmaceutical composition is present in an amount of about 6 µg to about 475 µg. In some aspects, the compound of Formula IA or pharmaceutically acceptable salt thereof in the pharmaceutical composition is present in an amount of about 6 µg to about 450 µg. In some aspects, the compound of Formula IA or pharmaceutically acceptable salt thereof in the pharmaceutical composition is present in an amount of about 7 µg to about 425 µg. In some aspects, the compound of Formula IA or pharmaceutically acceptable salt thereof in the pharmaceutical composition is present in an amount of about 7 µg to about 400 µg. In some aspects, the compound of Formula IA or pharmaceutically acceptable salt thereof in the pharmaceutical composition is present in an amount of about 8 µg to about 375 µg. In some aspects, the compound of Formula IA or pharmaceutically acceptable salt thereof in the pharmaceutical composition is present in an amount of about 8 µg to about 350 µg. In some aspects, the compound of Formula IA or pharmaceutically acceptable salt thereof in the pharmaceutical composition is present in an amount of about 9 µg to about 325 µg. In some aspects, the compound of Formula IA or pharmaceutically acceptable salt thereof in the pharmaceutical composition is present in an amount of about 9 µg to about 300 µg. In some aspects, the compound of Formula IA or pharmaceutically acceptable salt thereof in the pharmaceutical composition is present in an amount of about 10 µg to about 275 µg. In some aspects, the compound of Formula IA or pharmaceutically acceptable salt thereof in the pharmaceutical composition is present in an amount of about 10 µg to about 250 µg. In some aspects, the compound of Formula IA or pharmaceutically acceptable salt thereof in the pharmaceutical composition is present in an amount of about 10 µg to about 225 µg. In some aspects, the compound of Formula IA or pharmaceutically acceptable salt thereof in the pharmaceutical composition is present in an amount of about 10 µg to about 200 µg. In some aspects, the compound of Formula IA or pharmaceutically acceptable salt thereof in the pharmaceutical composition is present in an amount of about 10 µg to about 175 µg. In some aspects, the compound of Formula IA or pharmaceutically acceptable salt thereof in the pharmaceutical composition is present in an amount of about 10 µg to about 150 µg. In some aspects, the compound of Formula IA or pharmaceutically acceptable salt thereof in the pharmaceutical composition is present in an amount of about 10 µg to about 125 µg. In some aspects, the compound of Formula IA or pharmaceutically acceptable salt thereof in the pharmaceutical composition is present in an amount of about 10 µg to about 100 µg. In some aspects, the compound of Formula IA or pharmaceutically acceptable salt thereof in the pharmaceutical composition is present in an amount of about 10 µg to about 90 µg. In some aspects, the compound of Formula IA or pharmaceutically acceptable salt thereof in the pharmaceutical composition is present in an amount of about 10 µg to about 80 µg. In some aspects, the compound of Formula IA or pharmaceutically acceptable salt thereof in the pharmaceutical composition is present in an amount of about 10 µg to about 70 µg. In some aspects, the compound of Formula IA or pharmaceutically acceptable salt thereof in the pharmaceutical composition is present in an amount of about 10 µg to about 60 µg. In some aspects, the compound of Formula IA or pharmaceutically acceptable salt thereof in the pharmaceutical composition is present in an amount of about 10 µg to about 50 µg. In some aspects, the compound of Formula IA or pharmaceutically acceptable salt thereof in the pharmaceutical composition is present in an amount of about 11 µg to about 50 µg. In some aspects, the compound of Formula IA or pharmaceutically acceptable salt thereof in the pharmaceutical composition is present in an amount of about 12 µg to about 50 µg. In some aspects, the compound of Formula IA or pharmaceutically acceptable salt thereof in the pharmaceutical composition is present in an amount of about 12.5 µg to about 50 µg.

In some aspects, the pharmaceutical composition comprising a compound of Formula IA or pharmaceutically acceptable salt thereof further comprises a gamma-secretase inhibitor selected from the group consisting of nirogacestat, or a pharmaceutically acceptable salt thereof, crenigacestat, or a pharmaceutically acceptable salt thereof, AL101, or a pharmaceutically acceptable salt thereof, AL102, or a pharmaceutically acceptable salt thereof, semagacestat, or a pharmaceutically acceptable salt thereof, avagacestat, or a pharmaceutically acceptable salt thereof, and ianabecestat, or a pharmaceutically acceptable salt thereof. In some aspects, the pharmaceutical composition comprising Formula IA further comprises nirogacestat, or pharmaceutically acceptable salt thereof. In some aspects, the pharmaceutical composition comprising Formula IA further comprises crenigacestat, or pharmaceutically acceptable salt thereof. In some aspects, the pharmaceutical composition comprising Formula IA further comprises AL101, or pharmaceutically acceptable salt thereof. In some aspects, the pharmaceutical composition comprising Formula IA further comprises AL102, or pharmaceutically acceptable salt thereof. In some aspects, the pharmaceutical composition comprising Formula IA further comprises semagacestat, or pharmaceutically acceptable salt thereof. In some aspects, the pharmaceutical composition comprising Formula IA further comprises avagacestat, or pharmaceutically acceptable salt thereof. In some aspects, the pharmaceutical composition comprising Formula IA further comprises ianabecestat, or pharmaceutically acceptable salt thereof. In some aspects, the pharmaceutical composition comprising a compound of Formula IA or pharmaceutically acceptable salt thereof further comprises nirogacestat hydrobromide. In some aspects, the pharmaceutical composition comprising a compound of Formula IA or pharmaceutically acceptable salt thereof further comprises nirogacestat dihydrobromide.

The disclosure further relates to a pharmaceutical composition comprising a compound which is a compound of Formula IB

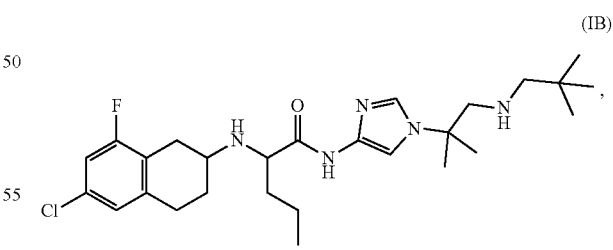

(IB)

or a pharmaceutically acceptable salt thereof. In some aspects, the compound of Formula IB or pharmaceutically acceptable salt thereof in the pharmaceutical composition is present in an amount of about 1 µg to about 500 µg. In some aspects, the compound of Formula IB or pharmaceutically acceptable salt thereof in the pharmaceutical composition is present in an amount of about 2 µg to about 500 µg. In some aspects, the compound of Formula IB or pharmaceutically acceptable salt thereof in the pharmaceutical composition is present in an amount of about 3 µg to about 500 µg. In some aspects, the compound of Formula IB or pharmaceutically acceptable salt thereof in the pharmaceutical composition is present in an amount of about 4 µg to about 500 µg. In some aspects, the compound of Formula IB or pharmaceutically acceptable salt thereof in the pharmaceutical composition is present in an amount of about 5 µg to about 500 µg. In some aspects, the compound of Formula IB or pharmaceutically acceptable salt thereof in the pharmaceutical composition is present in an amount of about 6 µg to about 475 µg. In some aspects, the compound of Formula IB or pharmaceutically acceptable salt thereof in the pharmaceutical composition is present in an amount of about 6 µg to about 450 µg. In some aspects, the compound of Formula IB or pharmaceutically acceptable salt thereof in the pharmaceutical composition is present in an amount of about 7 µg to about 425 µg. In some aspects, the compound of Formula IB or pharmaceutically acceptable salt thereof in the pharmaceutical composition is present in an amount of about 7 µg to about 400 µg. In some aspects, the compound of Formula IB or pharmaceutically acceptable salt thereof in the pharmaceutical composition is present in an amount of about 8 µg to about 375 µg. In some aspects, the compound of Formula IB or pharmaceutically acceptable salt thereof in the pharmaceutical composition is present in an amount of about 8 µg to about 350 µg. In some aspects, the compound of Formula IB or pharmaceutically acceptable salt thereof in the pharmaceutical composition is present in an amount of about 9 µg to about 325 µg. In some aspects, the compound of Formula IB or pharmaceutically acceptable salt thereof in the pharmaceutical composition is present in an amount of about 9 µg to about 300 µg. In some aspects, the compound of Formula IB or pharmaceutically acceptable salt thereof in the pharmaceutical composition is present in an amount of about 10 µg to about 275 µg. In some aspects, the compound of Formula IB or pharmaceutically acceptable salt thereof in the pharmaceutical composition is present in an amount of about 10 µg to about 250 µg. In some aspects, the compound of Formula IB or pharmaceutically acceptable salt thereof in the pharmaceutical composition is present in an amount of about 10 µg to about 225 µg. In some aspects, the compound of Formula IB or pharmaceutically acceptable salt thereof in the pharmaceutical composition is present in an amount of about 10 µg to about 200 µg. In some aspects, the compound of Formula IB or pharmaceutically acceptable salt thereof in the pharmaceutical composition is present in an amount of about 10 µg to about 175 µg. In some aspects, the compound of Formula IB or pharmaceutically acceptable salt thereof in the pharmaceutical composition is present in an amount of about 10 µg to about 150 µg. In some aspects, the compound of Formula IB or pharmaceutically acceptable salt thereof in the pharmaceutical composition is present in an amount of about 10 µg to about 125 µg. In some aspects, the compound of Formula IB or pharmaceutically acceptable salt thereof in the pharmaceutical composition is present in an amount of about 10 µg to about 100 µg. In some aspects, the compound of Formula IB or pharmaceutically acceptable salt thereof in the pharmaceutical composition is present in an amount of about 10 µg to about 90 µg. In some aspects, the compound of Formula IB or pharmaceutically acceptable salt thereof in the pharmaceutical composition is present in an amount of about 10 µg to about 80 µg. In some aspects, the compound of Formula IB or pharmaceutically acceptable salt thereof in the pharmaceutical composition is present in an amount of about 10 µg to about 70 µg. In some aspects, the compound of Formula IB or pharmaceutically acceptable salt thereof in the pharmaceutical composition is present in an amount of about 10 µg to about 60 µg. In some aspects, the compound of Formula IB or pharmaceutically acceptable salt thereof in the pharmaceutical composition is present in an amount of about 10 µg to about 50 µg. In some aspects, the compound of Formula IB or pharmaceutically acceptable salt thereof in the pharmaceutical composition is present in an amount of about 11 µg to about 50 µg. In some aspects, the compound of Formula IB or pharmaceutically acceptable salt thereof in the pharmaceutical composition is present in an amount of about 12 µg to about 50 µg. In some aspects, the compound of Formula IB or pharmaceutically acceptable salt thereof in the pharmaceutical composition is present in an amount of about 12.5 µg to about 50 µg.

In some aspects, the pharmaceutical composition comprising a compound of Formula IB further comprises a gamma-secretase inhibitor selected from the group consisting of nirogacestat, or a pharmaceutically acceptable salt thereof, crenigacestat, or a pharmaceutically acceptable salt thereof, AL101, or a pharmaceutically acceptable salt thereof, AL102, or a pharmaceutically acceptable salt thereof, semagacestat, or a pharmaceutically acceptable salt thereof, avagacestat, or a pharmaceutically acceptable salt thereof, and ianabecestat, or a pharmaceutically acceptable salt thereof. In some aspects, the pharmaceutical composition comprising a compound of Formula IB further comprises nirogacestat, or pharmaceutically acceptable salt thereof. In some aspects, the pharmaceutical composition comprising a compound of Formula IB further comprises crenigacestat, or pharmaceutically acceptable salt thereof. In some aspects, the pharmaceutical composition comprising a compound of Formula IB further comprises AL101, or pharmaceutically acceptable salt thereof. In some aspects, the pharmaceutical composition comprising a compound of Formula IB further comprises AL102, or pharmaceutically acceptable salt thereof. In some aspects, the pharmaceutical composition comprising a compound of Formula IB further comprises semagacestat, or pharmaceutically acceptable salt thereof. In some aspects, the pharmaceutical composition comprising a compound of Formula IB further comprises avagacestat, or pharmaceutically acceptable salt thereof. In some aspects, the pharmaceutical composition comprising a compound of Formula IB further comprises ianabecestat, or pharmaceutically acceptable salt thereof. In some aspects, the pharmaceutical composition comprising a compound of Formula IB or pharmaceutically acceptable salt thereof further comprises nirogacestat hydrobromide. In some aspects, the pharmaceutical composition comprising a compound of Formula IB or pharmaceutically acceptable salt thereof further comprises nirogacestat dihydrobromide.

The disclosure further relates to a pharmaceutical composition comprising a compound which is a compound of Formula IC

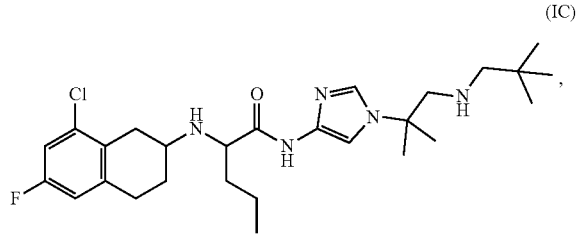

(IC)

or a pharmaceutically acceptable salt thereof. In some aspects, the compound of Formula IC or pharmaceutically acceptable salt thereof in the pharmaceutical composition is present in an amount of about 1 µg to about 500 µg. In some aspects, the compound of Formula IC or pharmaceutically acceptable salt thereof in the pharmaceutical composition is present in an amount of about 2 µg to about 500 µg. In some aspects, the compound of Formula IC or pharmaceutically acceptable salt thereof in the pharmaceutical composition is present in an amount of about 3 µg to about 500 µg. In some aspects, the compound of Formula IC or pharmaceutically acceptable salt thereof in the pharmaceutical composition is present in an amount of about 4 µg to about 500 µg. In some aspects, the compound of Formula IC or pharmaceutically acceptable salt thereof in the pharmaceutical composition is present in an amount of about 5 µg to about 500 µg. In some aspects, the compound of Formula IC or pharmaceutically acceptable salt thereof in the pharmaceutical composition is present in an amount of about 6 µg to about 475 µg. In some aspects, the compound of Formula IC or pharmaceutically acceptable salt thereof in the pharmaceutical composition is present in an amount of about 6 µg to about 450 µg. In some aspects, the compound of Formula IC or pharmaceutically acceptable salt thereof in the pharmaceutical composition is present in an amount of about 7 µg to about 425 µg. In some aspects, the compound of Formula IC or pharmaceutically acceptable salt thereof in the pharmaceutical composition is present in an amount of about 7 µg to about 400 µg. In some aspects, the compound of Formula IC or pharmaceutically acceptable salt thereof in the pharmaceutical composition is present in an amount of about 8 µg to about 375 µg. In some aspects, the compound of Formula IC or pharmaceutically acceptable salt thereof in the pharmaceutical composition is present in an amount of about 8 µg to about 350 µg. In some aspects, the compound of Formula IC or pharmaceutically acceptable salt thereof in the pharmaceutical composition is present in an amount of about 9 µg to about 325 µg. In some aspects, the compound of Formula IC or pharmaceutically acceptable salt thereof in the pharmaceutical composition is present in an amount of about 9 µg to about 300 µg. In some aspects, the compound of Formula IC or pharmaceutically acceptable salt thereof in the pharmaceutical composition is present in an amount of about 10 µg to about 275 µg. In some aspects, the compound of Formula IC or pharmaceutically acceptable salt thereof in the pharmaceutical composition is present in an amount of about 10 µg to about 250 µg. In some aspects, the compound of Formula IC or pharmaceutically acceptable salt thereof in the pharmaceutical composition is present in an amount of about 10 µg to about 225 µg. In some aspects, the compound of Formula IC or pharmaceutically acceptable salt thereof in the pharmaceutical composition is present in an amount of about 10 µg to about 200 µg. In some aspects, the compound of Formula IC or pharmaceutically acceptable salt thereof in the pharmaceutical composition is present in an amount of about 10 µg to about 175 µg. In some aspects, the compound of Formula IC or pharmaceutically acceptable salt thereof in the pharmaceutical composition is present in an amount of about 10 µg to about 150 µg. In some aspects, the compound of Formula IC or pharmaceutically acceptable salt thereof in the pharmaceutical composition is present in an amount of about 10 µg to about 125 µg. In some aspects, the compound of Formula IC or pharmaceutically acceptable salt thereof in the pharmaceutical composition is present in an amount of about 10 µg to about 100 µg. In some aspects, the compound of Formula IC or pharmaceutically acceptable salt thereof in the pharmaceutical composition is present in an amount of about 10 µg to about 90 µg. In some aspects, the compound of Formula IC or pharmaceutically acceptable salt thereof in the pharmaceutical composition is present in an amount of about 10 µg to about 80 µg. In some aspects, the compound of Formula IC or pharmaceutically acceptable salt thereof in the pharmaceutical composition is present in an amount of about 10 µg to about 70 µg. In some aspects, the compound of Formula IC or pharmaceutically acceptable salt thereof in the pharmaceutical composition is present in an amount of about 10 µg to about 60 µg. In some aspects, the compound of Formula IC or pharmaceutically acceptable salt thereof in the pharmaceutical composition is present in an amount of about 10 µg to about 50 µg. In some aspects, the compound of Formula IC or pharmaceutically acceptable salt thereof in the pharmaceutical composition is present in an amount of about 11 µg to about 50 µg. In some aspects, the compound of Formula IC or pharmaceutically acceptable salt thereof in the pharmaceutical composition is present in an amount of about 12 µg to about 50 µg. In some aspects, the compound of Formula IC or pharmaceutically acceptable salt thereof in the pharmaceutical composition is present in an amount of about 12.5 µg to about 50 µg.

In some aspects, the pharmaceutical composition comprising a compound of Formula IC further comprises a gamma-secretase inhibitor selected from the group consisting of nirogacestat, or a pharmaceutically acceptable salt thereof, crenigacestat, or a pharmaceutically acceptable salt thereof, AL101, or a pharmaceutically acceptable salt thereof, AL102, or a pharmaceutically acceptable salt thereof, semagacestat, or a pharmaceutically acceptable salt thereof, avagacestat, or a pharmaceutically acceptable salt thereof, and ianabecestat, or a pharmaceutically acceptable salt thereof. In some aspects, the pharmaceutical composition comprising a compound of Formula IC further comprises nirogacestat, or pharmaceutically acceptable salt thereof. In some aspects, the pharmaceutical composition comprising a compound of Formula IC further comprises crenigacestat, or pharmaceutically acceptable salt thereof. In some aspects, the pharmaceutical composition comprising a compound of Formula IC further comprises AL101, or pharmaceutically acceptable salt thereof. In some aspects, the pharmaceutical composition comprising a compound of Formula IC further comprises AL102, or pharmaceutically acceptable salt thereof. In some aspects, the pharmaceutical composition comprising a compound of Formula IC further comprises semagacestat, or pharmaceutically acceptable salt thereof. In some aspects, the pharmaceutical composition comprising a compound of Formula IC further comprises avagacestat, or pharmaceutically acceptable salt thereof. In some aspects, the pharmaceutical composition comprising a compound of Formula IC further comprises ianabecestat, or pharmaceutically acceptable salt thereof. In some aspects, the pharmaceutical composition comprising a compound of Formula IC or pharmaceutically acceptable salt thereof further comprises nirogacestat hydrobromide. In some aspects, the pharmaceutical composition comprising a compound of Formula IC or pharmaceutically acceptable salt thereof further comprises nirogacestat dihydrobromide.

In some aspects, the compound of Formula I, Formula IA, Formula IB, and Formula IC in the pharmaceutical composition is in the free base form.

In some aspects, the compound of Formula I, Formula IA, Formula IB, and Formula IC in the pharmaceutical composition is in a pharmaceutically acceptable salt form. In some aspects, the pharmaceutically acceptable salt form of the compound of Formula I, Formula IA, Formula IB, and Formula IC in the pharmaceutical composition is a hydrobromide salt form. In some aspects, the pharmaceutically acceptable salt form of the compound of Formula I, Formula IA, Formula IB, and Formula IC in the pharmaceutical composition is a dihydrobromide salt form.

In some aspects, the pharmaceutical composition comprising the compound of Formula I is an oral tablet that additionally comprises a pharmaceutically acceptable carrier. For oral administration, known carriers can be included in the pharmaceutical composition. For example, microcrystalline cellulose, sodium citrate, calcium carbonate, dicalcium phosphate and glycine may be employed along with various disintegrants such as starch (preferably corn, potato or tapioca starch), methylcellulose, alginic acid and certain complex silicates, together with granulation binders such as polyvinylpyrrolidone, sucrose, gelatin and acacia, can be included in a tablet. Additionally, lubricating agents such as magnesium stearate, sodium lauryl sulfate and talc are often useful for tabletting purposes. Solid compositions of a similar type may also be employed as fillers in gelatin capsules. Preferred materials in this connection include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions containing Compound 1 can be prepared in either sesame or peanut oil, in aqueous propylene glycol, or in sterile water or saline. The aqueous solutions should be suitably buffered (preferably pH greater than 8) if necessary and the liquid diluent first rendered isotonic with sufficient saline or glucose. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

In one aspect, the tablet comprises the compound of Formula I and about 25 mg to about 400 mg of nirogacestat, or pharmaceutically acceptable salt thereof. In one aspect, the tablet comprises about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 225 mg, about 250 mg, about 275 mg, about 300 mg, about 325 mg, about 350 mg, about 375 mg, or about 400 mg of nirogacestat, or a pharmaceutically acceptable salt thereof. In one aspect, the tablet comprises about 50 mg of nirogacestat, or a pharmaceutically acceptable salt thereof. In one aspect, the tablet comprises about 100 mg of nirogacestat, or a pharmaceutically acceptable salt thereof. In one aspect, the tablet comprises about 150 mg of nirogacestat, or pharmaceutically acceptable salt thereof.

In one aspect, the tablet comprises the compound of Formula I and about 25 mg to about 400 mg of nirogacestat hydrobromide. In one aspect, the tablet comprises about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 225 mg, about 250 mg, about 275 mg, about 300 mg, about 325 mg, about 350 mg, about 375 mg, or about 400 mg of nirogacestat hydrobromide. In one aspect, the tablet comprises about 50 mg of nirogacestat hydrobromide. In one aspect, the tablet comprises about 100 mg of nirogacestat hydrobromide. In one aspect, the tablet comprises about 150 mg of nirogacestat hydrobromide.

In one aspect, the tablet comprises the compound of Formula I and about 25 mg to about 400 mg of nirogacestat dihydrobromide. In one aspect, the tablet comprises about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 225 mg, about 250 mg, about 275 mg, about 300 mg, about 325 mg, about 350 mg, about 375 mg, or about 400 mg of nirogacestat dihydrobromide. In one aspect, the tablet comprises about 50 mg of nirogacestat dihydrobromide. In one aspect, the tablet comprises about 100 mg of nirogacestat dihydrobromide. In one aspect, the tablet comprises about 150 mg of nirogacestat dihydrobromide.

IV. Methods of Treatment

The pharmaceutical composition comprising a compound of Formula I can be administered to modulate or inhibit the Notch signaling pathway in organisms, including humans. Notch signaling is frequently elevated in a variety of human tumors (including, but not limited to breast, prostate, pancreas and T-cell acute lymphoblastic leukemia). Accordingly, the pharmaceutical composition comprising a compound of Formula I can be administered to treat a subject with tumors or cancer, including, but not limited to desmoid tumors, multiple myeloma, adenoid cystic carcinoma, and T-cell acute lymphoblastic leukemia. In one aspect, the pharmaceutical composition comprising a compound of Formula I can be administered to treat a subject with tumors or cancer, including, but not limited to desmoid tumors, multiple myeloma, adenoid cystic carcinoma, and T-cell acute lymphoblastic leukemia. In one aspect, the pharmaceutical composition comprising a compound of Formula I is administered to treat a subject having tumors, including desmoid tumors. In one aspect, the pharmaceutical composition comprising a compound of Formula I is administered to treat a subject with a cancer having a mutation in a Notch pathway gene. In one aspect, the pharmaceutical composition comprising a compound of Formula I is administered to treat a subject having multiple myeloma. In some aspects, the pharmaceutical composition comprising a compound of Formula I is administered to treat a subject having adenoid cystic carcinoma. In some aspects, the pharmaceutical composition comprising a compound of Formula I is administered to treat a subject having T-cell acute lymphoblastic leukemia.

EXAMPLES

The following synthetic examples are illustrative, but not limiting, of the methods described herein. Other suitable modifications and adaptations of the variety of conditions and parameters normally encountered in the field, and which are obvious to those skilled in the art, are within the spirit and scope of the invention.

Synthetic Example 1

2-(2-chloro-4-fluorophenyl)acetic acid is reacted with oxalyl chloride in dichloromethane at 0° C. in the presence of dimethylformamide. The resulting acid chloride is reacted with aluminum chloride and ethylene gas at 0° C. After quenching the mixture with water, the dichloromethane solution is distilled and replaced with tert-butyl methyl ether. The resulting slurry is cooled to 0° C. and filtered to isolate 8-chloro-6-fluoro-3,4-dihydronaphthalen-2(1H)-one.

Synthetic Example 2

8-chloro-6-fluoro-3,4-dihydronaphthalen-2(1H)-one is added to a phosphate buffer solution (pH 7-8) and reacted with isopropylamine in the presence of an amino transaminase and pyridoxal-5-phosphate monohydrate at 25° C. The resulting phosphoric acid salt is filtered and washed with acetone to isolate (S)-8-chloro-6-fluoro-1,2,3,4-tetrahydronaphthalen-2-amine phosphoric acid salt.

Synthetic Example 3

(S)-8-chloro-6-fluoro-1,2,3,4-tetrahydronaphthalen-2-amine phosphoric acid salt is added to tert-butyl methyl ether and then freebased with aqueous sodium hydroxide. The tert-butyl methyl ether is then removed by distillation and replaced with dichloromethane. Tert-butyl (R)-2-hydroxypentanoate is dissolved in dichloromethane with N,N-diisopropylethylamine and then reacted with triflouromethanesulfonic anhydride at −25° C. The resulting triflate is reacted with the freebase amine dichloromethane solution in the presence of N,N-diisopropylethylamine at 25° C. The mixture is quenched with aqueous potassium carbonate and the dichloromethane is removed by distillation and replaced with 1,4-dioxane. Hydrogen chloride solution in 1,4-dioxane is added to the mixture and the resulting hydrochloride salt is filtered and rinsed with 1,4-dioxane to isolate (S)-tert-butyl-2-(((S)-8-chloro-6-fluoro-1,2,3,4-tetrahydronaphthalen-2-yl)amino)pentanoate hydrochloride.

Synthetic Example 4

(S)-tert-butyl-2-(((S)-8-chloro-6-fluoro-1,2,3,4-tetrahydronaphthalen-2-yl)amino)pentanoate hydrochloride is added to a mixture of isopropanol and water and reacted with hydrochloric acid at 60° C. After the reaction is complete, the mixture is adjusted to a pH of ~7.0 with aqueous sodium hydroxide. The resulting slurry is filtered and washed with isopropanol to isolate (S)-2-(((S)-8-chloro-6-fluoro-1,2,3,4-tetrahydronaphthalen-2-yl)amino)pentanoic acid.

Synthetic Example 5

(S)-2-(((S)-8-chloro-6-fluoro-1,2,3,4-tetrahydronaphthalen-2-yl)amino)pentanoic acid is added to acetonitrile and pyridine hydrobromide and reacted with N,N-Carbonyldiimidazole at 25° C. After the reaction is complete, triethylamine is added to the mixture. 1-(2-methyl-1-(neopentylamino)propan-2-yl)-1H-imidazol-4-amine dihydrobromide is added to acetonitrile, cooled to −8° C., and freebased with triethylamine. The N,N-Carbonyldiimidazole reaction mixture is added to the freebased 1-(2-methyl-1-(neopentylamino)propan-2-yl)-1H-imidazol-4-amine mixture and reacted at −8° C. After reaction completion, hydrobromic acid is added at 40° C. and the resulting solution is adjusted to pH 2.8 with triethylamine. The resulting slurry is filtered and washed with acetonitrile to isolate (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide. (S)-2-(((S)-8-chloro-6-fluoro-1,2,3,4-tetrahydronaphthalen-2-yl)amino)-N-(1-(2-methyl-1-(neopentylamino)propan-2-yl)-1H-imidazol-4-yl) pentanamide dihydrobromide was further purified through crystallization by dissolving in ethanol and water with hydrobromic acid followed by addition of triethylamine. The resulting slurry was cooled, filtered, and rinsed with ethanol. Analytical Data: $^1$H NMR (400 MHz, DMSO-$d_6$): 11.33 (s, 1H), 9.35 (bd, 2H), 7.95 (bd, 2H), 7.76 (s, 1H), 7.55 (s, 1H), 7.32 (d, 1H), 7.06 (d, 1H), 4.24 (m, 1H), 3.50 (m, 3H), 3.31 (m, 1H), 2.92 (m, 1H), 2.80 (m, 2H), 2.55 (m, 2H), 2.19 (m, 1H), 1.85 (m, 3H), 1.64 (d, 6H), 1.31 (m, 2H), 0.91 (t, 3H), 0.87 (s, 9H); MS m/z: 506.30 (M+H).

Synthetic Example 6

2-(4-chloro-2-fluorophenyl)acetic acid is reacted with oxalyl chloride in dichloromethane at 0° C. in the presence of dimethylformamide. The resulting acid chloride is reacted with aluminum chloride and ethylene gas at 0° C. After quenching the mixture with water, the dichloromethane solution is distilled and replaced with tert-butyl methyl ether. The resulting slurry is cooled to 0° C. and filtered to isolate 6-chloro-8-fluoro-3,4-dihydronaphthalen-2(1H)-one.

Synthetic Example 7

6-chloro-8-fluoro-3,4-dihydronaphthalen-2(1H)-one is added to a phosphate buffer solution (pH 7-8) and reacted with isopropylamine in the presence of an amino transaminase and pyridoxal-5-phosphate monohydrate at 25° C. The resulting phosphoric acid salt is filtered and washed with acetone to isolate (S)-6-chloro-8-fluoro-1,2,3,4-tetrahydronaphthalen-2-amine phosphoric acid salt.

Synthetic Example 8

(S)-6-chloro-8-fluoro-1,2,3,4-tetrahydronaphthalen-2-amine phosphoric acid salt is added to tert-butyl methyl ether and then freebased with aqueous sodium hydroxide. The tert-butyl methyl ether is then removed by distillation and replaced with dichloromethane. Tert-butyl (R)-2-hydroxypentanoate is dissolved in dichloromethane with N,N-diisopropylethylamine and then reacted with triflouromethanesulfonic anhydride at −25° C. The resulting triflate is reacted with the freebase amine dichloromethane solution in the presence of N,N-diisopropylethylamine at 25° C. The mixture is quenched with aqueous potassium carbonate and the dichloromethane is removed by distillation and replaced with 1,4-dioxane. Hydrogen chloride solution in 1,4-dioxane is added to the mixture and the resulting hydrochloride salt is filtered and rinsed with 1,4-dioxane to isolate (S)-tert-butyl-2-(((S)-6-chloro-8-fluoro-1,2,3,4-tetrahydronaphthalen-2-yl)amino)pentanoate hydrochloride.

Synthetic Example 9

(S)-tert-butyl-2-(((S)-6-chloro-8-fluoro-1,2,3,4-tetrahydronaphthalen-2-yl)amino)pentanoate hydrochloride is added to a mixture of isopropanol and water and reacted with hydrochloric acid at 60° C. After the reaction is complete, the mixture is adjusted to a pH of ~7.0 with aqueous sodium hydroxide. The resulting slurry is filtered and washed with isopropanol to isolate (S)-2-(((S)-6-chloro-8-fluoro-1,2,3,4-tetrahydronaphthalen-2-yl)amino)pentanoic acid.

Synthetic Example 10

(S)-2-(((S)-6-chloro-8-fluoro-1,2,3,4-tetrahydronaphthalen-2-yl)amino)pentanoic acid is added to acetonitrile and pyridine hydrobromide and reacted with N,N-Carbonyldiimidazole at 25° C. After the reaction is complete, triethylamine is added to the mixture. 1-(2-methyl-1-(neopentylamino)propan-2-yl)-1H-imidazol-4-amine dihydrobromide is added to acetonitrile, cooled to −8° C., and freebased with triethylamine. The N,N-Carbonyldiimidazole reaction mixture is added to the freebased 1-(2-methyl-1-(neopentylamino)propan-2-yl)-1H-imidazol-4-amine mixture and reacted at −8° C. After reaction completion, hydrobromic acid is added at 40° C. and the resulting solution is adjusted to pH 2.8 with triethylamine. The resulting slurry is filtered and washed with acetonitrile to isolate (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide. (S)-2-(((S)-6-chloro-8-fluoro-1,2,3,4-tetrahydronaphthalen-2-yl)amino)-N-(1-(2-methyl-1-(neopentylamino)propan-2-yl)-1H-imidazol-4-yl) pentanamide dihydrobromide was further purified through crystallization by dissolving in ethanol and water with hydrobromic acid followed by addition of triethylamine. The resulting slurry was cooled, filtered, and rinsed with ethanol. Analytical Data: $^1$H NMR (400 MHz, DMSO-d$_6$): 11.30 (s, 1H), 9.63 (bs, 1H), 9.38 (bs, 1H), 8.20 (bs, 2H), 7.77 (s, 1H), 7.56 (s, 1H), 7.24 (d, 1H), 7.10 (s, 1H), 4.27 (m, 1H), 3.65 (m, 3H), 3.53 (m, 2H), 3.28 (m, 1H), 2.95 (m, 1H), 2.83 (m, 2H), 2.25 (m, 1H), 1.88 (m, 3H), 1.66 (d, 6H), 1.33 (m, 2H), 0.90 (t, 3H), 0.86 (s, 9H); MS m/z: 506.30 (M+H).

Synthetic Example 11

2-(3-chloro-4-fluorophenyl)acetic acid is reacted with oxalyl chloride in dichloromethane at 0° C. in the presence of dimethylformamide. The resulting acid chloride is reacted with aluminum chloride and ethylene gas at 0° C. After quenching the mixture with water, the dichloromethane solution is distilled and replaced with tert-butyl methyl ether. The resulting slurry is cooled to 0° C. and filtered to isolate 7-chloro-6-fluoro-3,4-dihydronaphthalen-2(1H)-one.

Synthetic Example 12

7-chloro-6-fluoro-3,4-dihydronaphthalen-2(1H)-one is added to a phosphate buffer solution (pH 7-8) and reacted with isopropylamine in the presence of an amino transaminase and pyridoxal-5-phosphate monohydrate at 25° C. The resulting phosphoric acid salt is filtered and washed with acetone to isolate (S)-7-chloro-6-fluoro-1,2,3,4-tetrahydronaphthalen-2-amine phosphoric acid salt.

Synthetic Example 13

(S)-7-chloro-6-fluoro-1,2,3,4-tetrahydronaphthalen-2-amine phosphoric acid salt is added to tert-butyl methyl ether and then freebased with aqueous sodium hydroxide. The tert-butyl methyl ether is then removed by distillation and replaced with dichloromethane. Tert-butyl (R)-2-hydroxypentanoate is dissolved in dichloromethane with N,N-diisopropylethylamine and then reacted with trifluromethanesulfonic anhydride at −25° C. The resulting triflate is reacted with the freebase amine dichloromethane solution in the presence of N,N-diisopropylethylamine at 25° C. The mixture is quenched with aqueous potassium carbonate and the dichloromethane is removed by distillation and replaced with 1,4-dioxane. Hydrogen chloride solution in 1,4-dioxane is added to the mixture and the resulting hydrochloride salt is filtered and rinsed with 1,4-dioxane to isolate (S)-tert-butyl-2-(((S)-7-chloro-6-fluoro-1,2,3,4-tetrahydronaphthalen-2-yl)amino)pentanoate hydrochloride.

Synthetic Example 14

(S)-tert-butyl-2-(((S)-7-chloro-6-fluoro-1,2,3,4-tetrahydronaphthalen-2-yl)amino)pentanoate hydrochloride is added to a mixture of isopropanol and water and reacted with hydrochloric acid at 60° C. After the reaction is complete, the mixture is adjusted to a pH of ~7.0 with aqueous sodium hydroxide. The resulting slurry is filtered and washed with isopropanol to isolate (S)-2-(((S)-7-chloro-6-fluoro-1,2,3,4-tetrahydronaphthalen-2-yl)amino)pentanoic acid.

Synthetic Example 15

(S)-2-(((S)-7-chloro-6-fluoro-1,2,3,4-tetrahydronaphthalen-2-yl)amino)pentanoic acid is added to acetonitrile and pyridine hydrobromide and reacted with N,N-Carbonyldiimidazole at 25° C. After the reaction is complete, triethylamine is added to the mixture. 1-(2-methyl-1-(neopentylamino)propan-2-yl)-1H-imidazol-4-amine dihydrobromide is added to acetonitrile, cooled to −8° C., and freebased with triethylamine. The N,N-Carbonyldiimidazole reaction mixture is added to the freebased 1-(2-methyl-1-(neopentylamino)propan-2-yl)-1H-imidazol-4-amine mixture and reacted at −8° C. After reaction completion, hydrobromic acid is added at 40° C. and the resulting solution is adjusted to pH 2.8 with triethylamine. The resulting slurry is filtered and washed with acetonitrile to isolate (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl)pentanamide dihydrobromide. (S)-2-(((S)-7-chloro-6-fluoro-1,2,3,4-tetrahydronaphthalen-2-yl)amino)-N-(1-(2-methyl-1-(neopentylamino)propan-2-yl)-1H-imidazol-4-yl) pentanamide dihydrobromide was further purified through crystallization by dissolving in ethanol and water with hydrobromic acid followed by addition of triethylamine. The resulting slurry was cooled, filtered, and rinsed with ethanol. Analytical Data: $^1$H NMR (400 MHz, DMSO-d$_6$): 11.25 (s, 1H), 9.41 (bs, 1H), 9.26 (bs, 1H), 8.06 (bs, 2H), 7.77 (s, 1H), 7.55 (s, 1H), 7.32 (d, 1H), 7.20 (d, 1H), 4.24 (m, 1H), 3.52 (m, 2H), 3.28 (m, 1H), 3.15 (m, 2H) 2.90 (m, 2H), 2.78 (m, 1H), 2.53 (m, 1H), 2.25 (m, 1H), 1.89 (m, 3H), 1.66 (d, 6H), 1.33 (m, 2H), 0.91 (t, 3H), 0.86 (s, 9H); MS m/z: 506.30 (M+H).

What is claimed is:

1. A method of treating a desmoid tumor in a patient in need thereof comprising administering a pharmaceutical composition comprising a compound of Formula IA

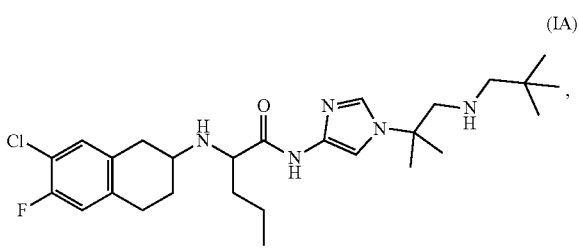

(IA)

or a pharmaceutically acceptable salt thereof.

2. The method of claim 1, wherein the compound of Formula IA or pharmaceutically acceptable salt thereof in the pharmaceutical composition is present in an amount of about 1 μg to about 200 μg.

3. The method of claim 1, wherein the compound of Formula IA or pharmaceutically acceptable salt thereof in the pharmaceutical composition is present in an amount of about 1 μg to about 150 μg.

4. The method of claim 1, wherein the compound of Formula IA or pharmaceutically acceptable salt thereof in the pharmaceutical composition is present in an amount of about 1 μg to about 100 μg.

5. The method of claim 1, wherein the compound of Formula IA or pharmaceutically acceptable salt thereof in the pharmaceutical composition is present in an amount of about 1 μg to about 50 μg.

6. The method of claim 1, wherein the pharmaceutical composition further comprises nirogacestat or a pharmaceutically acceptable salt thereof.

7. The method of claim 6, wherein the compound of Formula IA or pharmaceutically acceptable salt thereof in the pharmaceutical composition is present in an amount of about 1 μg to about 200 μg.

8. The method of claim 7, wherein the pharmaceutical composition comprises 50 mg nirogacestat or a pharmaceutically acceptable salt thereof.

9. The method of claim 6, wherein the compound of Formula IA or pharmaceutically acceptable salt thereof in the pharmaceutical composition is present in an amount of about 1 μg to about 150 μg.

10. The method of claim 9, wherein the pharmaceutical composition comprises 50 mg nirogacestat or a pharmaceutically acceptable salt thereof.

11. The method of claim 6, wherein the compound of Formula IA or pharmaceutically acceptable salt thereof in the pharmaceutical composition is present in an amount of about 1 μg to about 100 μg.

12. The method of claim 11, wherein the pharmaceutical composition comprises 50 mg nirogacestat or a pharmaceutically acceptable salt thereof.

13. The method of claim 6, wherein the compound of Formula IA or pharmaceutically acceptable salt thereof in the pharmaceutical composition is present in an amount of about 1 μg to about 50 μg.

14. The method of claim 13, wherein the pharmaceutical composition comprises 50 mg nirogacestat or a pharmaceutically acceptable salt thereof.

\* \* \* \* \*